(12) United States Patent
Gross

(10) Patent No.: US 8,897,855 B2
(45) Date of Patent: Nov. 25, 2014

(54) MEDICAL IMAGING METHOD AND SYSTEM

(71) Applicant: Patrick Gross, Langensendelbach (DE)

(72) Inventor: Patrick Gross, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 145 days.

(21) Appl. No.: 13/671,632

(22) Filed: Nov. 8, 2012

(65) Prior Publication Data

US 2013/0116542 A1 May 9, 2013

(30) Foreign Application Priority Data

Nov. 8, 2011 (DE) .......................... 10 2011 085 894

(51) Int. Cl.
*A61B 8/08* (2006.01)
*A61B 5/055* (2006.01)
*A61B 5/00* (2006.01)
*A61B 8/13* (2006.01)
*A61B 8/14* (2006.01)

(52) U.S. Cl.
CPC ............... *A61B 8/5261* (2013.01); *A61B 5/055* (2013.01); *A61B 5/0035* (2013.01); *A61B 8/13* (2013.01); *A61B 8/14* (2013.01); *A61B 8/485* (2013.01)
USPC ........... 600/411; 600/407; 600/424; 600/431; 600/437; 600/440; 600/442; 600/476; 382/128; 382/131

(58) Field of Classification Search
CPC ........ A61B 5/0035; A61B 5/055; A61B 8/13; A61B 8/14; A61B 8/485
USPC ......... 600/411, 424, 431, 437, 438, 440, 442; 382/128, 131
See application file for complete search history.

(56) References Cited

U.S. PATENT DOCUMENTS

| | | | |
|---|---|---|---|
| 5,769,790 A | 6/1998 | Watkins et al. | |
| 8,187,187 B2 | 5/2012 | Fan et al. | |
| 8,233,681 B2 * | 7/2012 | Aylward et al. | 382/128 |
| 2004/0234113 A1 * | 11/2004 | Miga | 382/128 |
| 2007/0016031 A1 * | 1/2007 | Mourad et al. | 600/437 |
| 2007/0167705 A1 * | 7/2007 | Chiang et al. | 600/407 |
| 2008/0039723 A1 * | 2/2008 | Suri et al. | 600/437 |

(Continued)

FOREIGN PATENT DOCUMENTS

WO 2008067905 A1 6/2008

OTHER PUBLICATIONS

Lazebnik et al., "Tissue Strain Analytics Virtual Touch Tissue Imaging and Quantification," Siemens ACUSON S2000 Ultrasound System (Oct. 2008).

*Primary Examiner* — Baisakhi Roy
(74) *Attorney, Agent, or Firm* — Schiff Hardin LLP (57) ABSTRACT

In an imaging procedure, sound pressure is generated by applying ultrasound to the region to be imaged in order to cause a deformation of tissue therein from at least one acquired ultrasound image data set, first data are determined that represent, with spatial resolution, the deformation of the tissue as a reaction to the sound pressure. At least one magnetic resonance image data set is acquired, from which second data are determined that represent, with spatial resolution, the deformation of the tissue as a reaction to the sound pressure. The at least one ultrasound image data set and the at least one magnetic resonance image data set are brought into registration with each other by a comparison of the first data and the second data.

22 Claims, 5 Drawing Sheets

(56) References Cited

U.S. PATENT DOCUMENTS

2008/0242979 A1 10/2008 Fisher et al.
2010/0087727 A1 4/2010 Gross
2010/0256504 A1* 10/2010 Moreau-Gaudry et al. .. 600/476
2011/0044521 A1* 2/2011 Tewfik et al. ................. 382/131
2012/0133663 A1* 5/2012 Tanigawa ..................... 345/581
2013/0046175 A1* 2/2013 Sumi ............................ 600/431
2013/0070074 A1* 3/2013 Won .............................. 348/77

* cited by examiner

MEDICAL IMAGING METHOD AND SYSTEM

BACKGROUND OF THE INVENTION

1. Field of the Invention

The invention concerns methods and devices for medical imaging. The invention in particular concerns such methods and devices with which a registration of images that were acquired with different imaging modalities is possible.

2. Description of the Prior Art

Several different imaging methods are used in medical engineering. Among these are, for example, computed tomography, magnetic resonance tomography, ultrasound and positron emission tomography. These imaging modalities deliver spatially resolved information about different physical properties of an examined region of an examination subject. Since different imaging modalities can provide information about different properties of the examined region, it is desirable to acquire image data with different imaging modalities.

In imaging of an examined region with multiple imaging modalities, the registration of different acquired images with respect to each other is a requirement. A registration requires that the images acquired with different imaging modalities be aligned and correctly scaled in a suitable manner. Due to the different physical processes on which the different imaging modalities are based, different perturbations can be present in the images acquired with different imaging modalities. For example, an image acquired with a magnetic resonance imaging device can have perturbations due to nonlinearities of gradient fields, with such perturbations not being present in an image of the same region that is acquired with an ultrasound imaging device.

For registration of images that have been acquired with different imaging modalities, user-defined anatomical landmarks can be identified in different images. For example, bones or catheters can be used as landmarks. However, such landmarks are linked to a position in the case of a bone, or in the case of the catheter can merely be invasively positioned and be dependent on the anatomy of the patient. A user-defined landmark establishment can be time-consuming. Depending on the experience of the user, a user-defined establishment can be imprecise or error-prone if the user cannot reliably identify anatomical landmarks. It can be difficult to determine a sufficiently high number of registration points in order to be able to produce a nonlinearity for registration in three dimensions. The number of anatomical landmarks that can easily be recognized in images may be too few for such purposes.

US 2010/0087727 A1 and DE 10 2008 047 644 A1 describe a method and a combination system in which a registration of images acquired with different imaging modalities is implemented depending on a thermal information. This requires a corresponding detectable heating of the examination subject.

There still exists a need for methods and devices for imaging in which a reliable co-registration of images acquired with different imaging modalities is possible in order to be able to fuse information acquired in the various image data with one another.

SUMMARY OF THE INVENTION

An object of the invention is to provide a method, a device and a system for imaging that allows a reliable registration of image data sets acquired with different imaging modalities. Furthermore, an object of the invention is to enable such registration using a number of registration points without the measurement of a temperature profile being required.

In a method according to the invention, sound pressure is generated by the application of ultrasound in order to cause a deformation of tissue of an examination subject. At least one ultrasound image data set is then acquired with an ultrasound imaging device. First data are determined depending on the at least one ultrasound image data set, the first data representing (with spatial resolution) the deformation of the tissue as a reaction to the sound pressure. At least one magnetic resonance image data set is acquired (also after the application of the sound pressure) with a magnetic resonance imaging device. Second data are determined depending on the at least one magnetic resonance image data set, the second data also representing (with spatial resolution) the deformation of the tissue as a reaction to the sound pressure. A registration of the at least one ultrasound image data set and the at least one magnetic resonance image data set is implemented by a comparison of the first data and second data, which is facilitated by the fact that the tissue has been deformed in each data set by the sound pressure.

In the method an ultrasound imaging and a magnetic resonance imaging are combined. Ultrasound and nuclear magnetic resonance show (make visible) different material properties. Through such a combined imaging, information about both the response of the examination subject to ultrasound and to the nuclear magnetic resonance dynamic can be obtained. Ultrasound and nuclear magnetic resonance have only slight or no mutual influences. This facilitates the combined imaging.

In the method, the incurred deformations or the reaction of the tissue of the examination subject serve as landmarks for the registration. Local landmarks can be generated by the imaging system without invasive procedures and by a suitable generation of the sound pressure. A high flexibility is thereby achieved. The number and density of the landmarks can be adjusted so that a nonlinear registration can be made with a desired precision.

The sound pressure can be generated in order to cause a local deformation of the tissue. The identification of suitable landmarks in the data acquired with ultrasound imaging and with magnetic resonance imaging is thereby facilitated. Localized deformations of the tissue that are chronologically sequential or chronologically parallel can be caused. Each of the deformations can have an extent that is smaller (in particular much smaller) than the region of the examination subject that is imaged with the imaging modalities.

The first data can be determined so that they represent a spatially dependent rigidity or viscosity of the tissue. Such first data can be determined simply and reliably, for example using ultrasound elastography or shear wave imaging. The rigidity or viscosity of the tissue quantifies the deformation of the tissue as a reaction to the sound pressure and can be used for co-registration.

The first data can also be determined so that the first data represent a spatially dependent shift of the tissue as a reaction to the sound pressure in a coordinate system of the at least one ultrasound image data set. For this purpose, the shift of the tissue can be determined with spatial dependency, for example depending on two ultrasound image data sets acquired in chronological sequence. Such a map of the deformation facilitates a comparison of images acquired with different imaging modalities.

The second data can be determined so that they second data represent a spatially dependent rigidity or viscosity of the tissue in a coordinate system of the at least one magnetic resonance image data set. The rigidity or viscosity of tissue can be detected, for example, by the combination of ultrasound to generate acoustic radiation pressure with a magnetic resonance imaging. In particular, diffusion-sensitive magnetic resonance imaging sequences can be used for this in order to make it possible to depict a viscous pulse transmission. The rigidity or viscosity of the tissue quantifies the deformation of the tissue as a reaction to the sound pressure and can be used for registration.

The second data can be determined so that the second data represent a spatially dependent shift of the tissue as a reaction to the sound pressure in a coordinate system of the at least one magnetic resonance image data set. For this purpose, the shift of the tissue can be determined with spatial dependency, for example depending on two magnetic resonance image data sets acquired in chronological sequence. Such a map of the deformation facilitates a comparison of images acquired with different imaging modalities.

Multiple (in particular more than three) registration points can be determined depending on the comparison of the first data and the second data. The registration can be a nonlinear registration. The registration can be based on a nonlinear perturbation or compression of the at least one magnetic resonance image data set and/or of the at least one ultrasound image data set. The registration can embody a shearing of the at least one magnetic resonance image data set and/or of the at least one ultrasound image data set.

The generation of the sound pressure by the application of ultrasound in order to cause a local deformation of the tissue can be implemented automatically depending on a desired number and/or density of registration points. The system for imaging can automatically select the number and/or density of registration points and accordingly automatically control the generation of the sound pressure via application of ultrasound. In this way it can be automatically ensured that a sufficient number and/or density of registration points is present for a nonlinear co-registration.

The generation of the sound pressure by the application of ultrasound in order to cause a local deformation of the tissue can take place depending on properties of the magnetic resonance imaging device. The generation of the sound pressure by the application of ultrasound in order to cause a local deformation of the tissue can take place depending on non-linearities in gradient fields of the magnetic resonance imaging device. In this way it can be ensured that a larger number of landmarks for registration is generated in regions in which the at least one magnetic resonance image data set exhibits a stronger perturbation than in regions in which gradient fields show a linear response.

A first magnetic resonance image data set and a second magnetic resonance image data set can be acquired with a temporal offset. The second data can be determined depending on a comparison of the first magnetic resonance image data set and the second magnetic resonance image data set. The first magnetic resonance image data set can be acquired before the generation of the sound pressure, and the second magnetic resonance image data set can be acquired during the generation of the sound pressure or after the generation of the sound pressure. The second data can be determined in that they represent a spatially dependent displacement of the tissue as a reaction to the sound pressure.

In the method, only one magnetic resonance image data set can also be acquired while the sound pressure is generated in order to cause the deformation of the tissue. The magnetic resonance image data set can be acquired with a diffusion-sensitive magnetic resonance imaging sequence. In this way a rigidity or viscosity of the tissue can be determined with spatial resolution without repeated imaging of the same voxel. This can be calibrated with the first data in order to implement the co-registration. A repeated scanning of the same voxel with subsequent difference calculation of multiple magnetic resonance image data sets can thus be avoided.

In the method, a first ultrasound image data set can be acquired before the generation of the sound pressure. A second ultrasound image data set can be acquired after or during the generation of the sound pressure that causes a local deformation of the tissue. The first data can be determined depending on a comparison of the first ultrasound image data set and the second ultrasound image data set. The first data can be determined so that they represent a spatially dependent displacement of the tissue as a reaction to the sound pressure and the local deformation that is thereby caused.

The sound pressure can be generated depending on a region of the examination subject that is selected for the acquisition of the at least one magnetic resonance image data set. For example, a direction and/or a focus of ultrasound that is generated by an ultrasound transducer for generation of the sound pressure can be established depending on operating parameters of the magnetic resonance imaging device. The direction of the ultrasound can be selected so that it corresponds to the direction in which the magnetic resonance imaging sequence is diffusion-sensitive. Given sequential readout of multiple slices of the examination subject with the magnetic resonance imaging device, a focus of the acoustic radiation generated by the ultrasound transducer can be adjusted so that it lies in the slice read out by the magnetic resonance imaging device and/or is separated from the slice read out by the magnetic resonance imaging device by less than a threshold.

According to a further exemplary embodiment of the invention, a non-transitory, computer-readable data storage medium is encoded with a command sequence that, upon execution by an electronic computer of an imaging system with a magnetic resonance imaging device and an ultrasound imaging device, causes the imaging system to implement at least one embodiment of the inventive method. For example, the storage medium can be loadable into the memory of an evaluation and control computer of the imaging system. The command sequence can be a source code or a compiled command sequence. With the command sequence, the imaging system can be programmatically configured to implement the method.

The data storage medium can be, for example, a CD-ROM, a DVD, a magnetic tape, a flash memory or a USB stick on which the command sequence is stored as electronically readable control information.

The invention also encompasses an electronic computer for imaging. The electronic computer has a first interface to receive at least one ultrasound image data set and a second interface to receive at least one magnetic resonance image data set. The electronic computer has a processor unit that is configured to determine first data depending on the at least one ultrasound image data set so that the first data represent a deformation of tissue of an examination subject as a reaction to sound pressure, with spatial resolution. The processor unit is configured to determine second data depending on the at least one magnetic resonance image data set so that the second data represent a deformation of tissue of an examination subject as a reaction to sound pressure, with spatial resolution. The processor unit is configured to implement a registration of the at least one ultrasound image data set and the at least one magnetic resonance image data set based on a comparison of the first data and the second data.

The invention also encompasses an imaging system that includes an ultrasound imaging device, a magnetic resonance imaging device and an electronic computer according to an exemplary embodiment, the electronic computer being in communication with the ultrasound imaging device and the magnetic resonance imaging device.

The electronic computer is configured to control an ultrasound transducer in order to generate the sound pressure via application of ultrasound. In this way the electronic computer can monitor the dynamic placement of landmarks that are generated by the deformation of tissue.

The electronic computer and of the imaging system have exemplary embodiments corresponding to the embodiments, and effects achieved thereby, of the method according to the invention.

DESCRIPTION OF THE PREFERRED EMBODIMENTS

Figure 1:
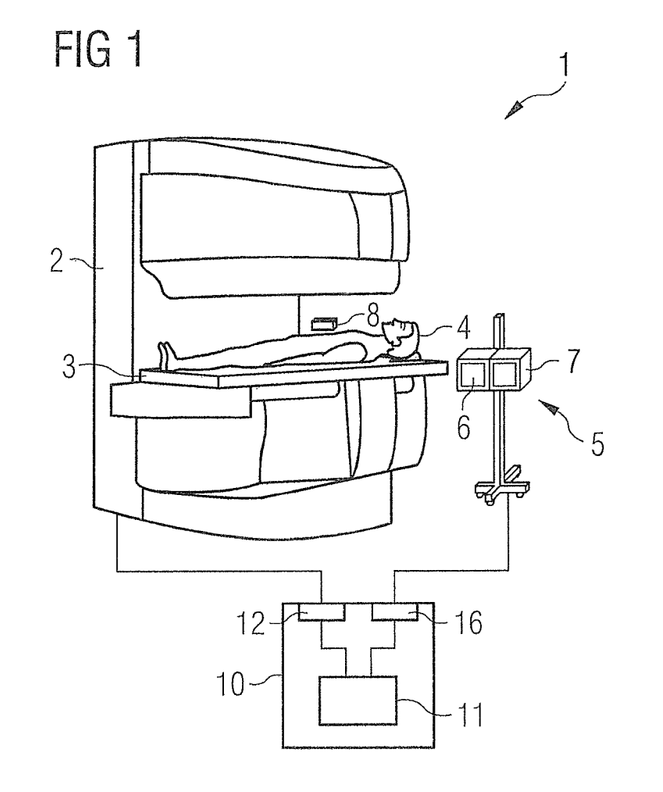
FIG. 1 schematically illustrates an imaging system in accordance with the invention.

FIG. 1 shows an imaging system 1 according to an exemplary embodiment of the invention. The imaging system 1 has a magnetic resonance (MR) imaging device 2 and an ultrasound system 5. The MR imaging device 2 has a support device 3 (for example an examination bed) on which an examination subject 4 is borne. The ultrasound system 5 can have an ultrasound (US) imaging device 6 and a US treatment device 7 that can be arranged in a common housing. The US treatment device 7 generates an ultrasound pulse with an amplitude so that the resulting sound pressure leads to a deformation of soft tissue of the examination subject 4. The amplitude can be selected so that the displacement of soft tissue in a patient amounts to one or a few micrometers. The displacement of soft tissue can be between one and twenty micrometers. Given the use of ultrasound pulses, such displacements of soft tissue can be achieved by operation in which conventional acoustic energies are not exceeded. Alternatively or in addition to the US treatment device 7 that is provided in a housing with the US imaging device 6, the ultrasound system 5 can have a separate US converter 8 in order to inject ultrasound into the examination subject and/or to detect ultrasound.

The MR imaging device 2 and the ultrasound system 5 have additional known elements that are not shown for clarity. For example, the MR imaging device 2 has at least one radio-frequency coil and a gradient system. In one embodiment, a component of the ultrasound system can be attached to a robot arm that can be moved relative to the MR imaging device 2. An automatic or user-defined positioning of the component of the ultrasound system 5 (which injects ultrasound into the examination subject 4) can take place via such a robot arm.

The imaging system 1 has an electronic computer 10 that is coupled with the MR imaging device 2 and the ultrasound system 5. The electronic computer 10 fulfills evaluation functions. As will be described in more detail, from at least one US image data set that is acquired with the US imaging device 6 the electronic computer 10 determines first data that represent a local deformation of tissue as a reaction to sound pressure generated with the ultrasound system. The first data can include the position of at least one point in a US image data set that has a maximum displacement relative to its position before application of the sound pressure. The first data can also include the positions of multiple local displacement or deformation maxima. The electronic computer 10 is furthermore configured to determine, from at least one MR image data set that is acquired with the MR imaging device 2, second data that represent a local deformation of tissue as a reaction to sound pressure generated with the ultrasound system. The second data can include the position of at least one point in an MR image data set that has a maximum displacement relative to its position before application of the sound pressure. The second data can also include the positions of multiple local displacement or deformation maxima in an MR image data set. The electronic computer 10 is configured to associate the registration points identified in such a manner with one another. The registration of MR image data sets and US image data sets takes place using the registration points identified in this manner.

The electronic computer 10 also fulfills control functions. Separate control and evaluation computers can be provided that individually perform the functions that the electronic computer 10 performs in combination. The electronic computer 10 can control the ultrasound system 5 so that sound pressure is generated that leads to a local deformation of tissue of the examination subject. The sound pressure can thus be generated so that an ultrasound pulse or multiple short ultrasound pulses are generated in order to cause the local deformation. The ultrasound pulse can have a duration of less than 500 microseconds, for example a duration in an interval from 50 to 150 microseconds. By using pulses that lead to a local displacement of tissue, the energy injection and a heating of the tissue can be kept low. The ultrasound pulse can be spatially focused. Displacements in the range of up to 20 micrometers (for example 1 to 20 micrometers) can be sufficient in order to be reliably identified in both US image data sets and MR image data sets. Such displacements can be achieved with conventional energies used by ultrasound systems. The ultrasound pulse that is generated by causing a local deformation can be generated so that a lateral expansion upon striking a predetermined tissue is less than a threshold.

The electronic computer 10 can be configured to determine a number and/or density of registration points. The electronic computer 10 can automatically establish the number and/or density, wherein the registration points do not need to be distributed homogenously. For example, the electronic computer 10 can automatically identify softer tissue using an overview image that is acquired with the MR imaging device 2 or with the US imaging device 5.

By means of sound pressure, a landmark in which a deformation of soft tissue is caused that is imaged both by the MR imaging device 2 and by the US imaging device 5 can respectively be generated dynamically in the image exposures that are implemented in parallel with the MR imaging device 2 and the US imaging device 5.

The electronic computer 10 can control the ultrasound system 5 to generate local deformations of the tissue depending on properties of the MR imaging device 2 and/or the ultrasound system 5. For example, gradient fields of the MR imaging device 2 can have nonlinearities that are more strongly expressed in some regions of the imaged region. In this case, the electronic computer 10 can control the ultrasound system 5 so that local deformations at tissue that serve as landmarks for the registration are set in these regions in a sufficient number and/or density in order to allow the implementation of a nonlinearity co-registration. For example, instead of a linear scaling of the MR image data a nonlinear scaling (i.e. a nonlinear compression or skewing) can take place. The parameters of the nonlinear scaling can be determined in that more than three registration points are set via local deformation. As an alternative or in addition to the registration, a shearing of the MR image data can be made. The parameters of the shearing can be determined by more than three registration points being set by means of local deformation.

The electronic computer 10 has a first interface 16 via which a processor unit 11 receives data from the ultrasound system 5. In the event that the electronic computer 10 also executes control functions, control commands can also be output to the ultrasound system 5 via the first interface 16. The generation of sound pressure via ultrasound to set a deformation mark can be controlled with the control commands. The electronic computer 10 has a second interface 12 via which the processor unit 11 receives data from the MR imaging device 2. In the event that the electronic computer 10 also executes control functions, control commands can also be output to the MR imaging device 2 via the second interface 12. The electronic computer 10 is designed so that the generation of sound pressure to set a deformation mark takes place coordinated in time with the imaging via the MR imaging device 2. The ultrasound system 5 can be controlled depending on a control signal that is used to control the MR imaging device 2. The ultrasound system 5 can be controlled so that a deformation in a slice or in a partial volume of the examination subject (which slice or partial volume is imaged with the MR imaging device 2) is caused by a generated pulse to locally deform the tissue. The processor unit 11 can be configured by programming so that the electronic computer 10 executes the various evaluation and control functions described here.

Figure 2:
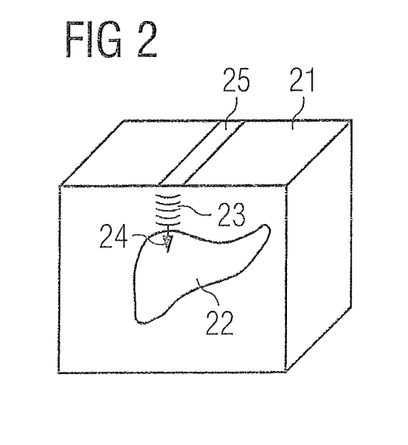
FIG. 2 and FIG. 3 show an examined region of an examination subject to explain the functioning of the imaging system.
Figure 3:
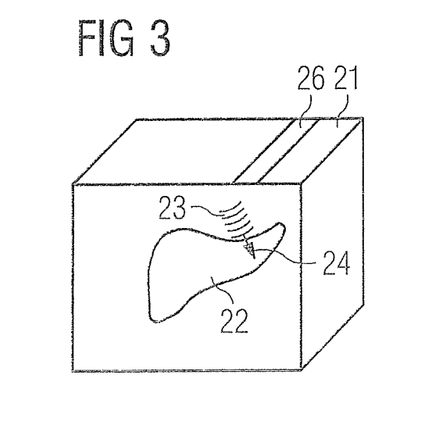

FIGS. 2 and 3 illustrate the use of sound pressure to dynamically generate deformations that serve as landmarks for a co-registration. FIG. 2 and FIG. 3 respectively show an examined region 21 of an examination subject. Tissue 22 that has a low rigidity is locally deformed by radiating an ultrasound pulse 23. Through viscous pulse transmission, a force is generated that results from a sound pressure 24 striking the tissue. The ultrasound pressure 23 generates a force generated via acoustic radiation. The force generated via acoustic radiation causes the local deformation of the tissue 22. The force generated by acoustic radiation or, respectively, the deformation of the tissue caused as a reaction to this is detected with both MR imaging and US imaging. The position of the deformed tissue is detected in a coordinate system of an MR image data set and in a coordinate system of a US image data set. A registration point is thereby provided. The process can be repeated chronologically in parallel or chronologically in sequence, wherein multiple local deformations are caused at different points of the examination subject.

The deformation that is caused by the sound pressure 24 can be produced so that it is imaged by the MR imaging device. In the event that the MR imaging at a specific point in time spatially selectively images a slice or a partial volume 25, the ultrasound pulse 23 can be generated so that a deformation is caused in the slice or the partial volume 25. In the event that the MR imaging images a different slice or a different partial volume 26 at another point in time, the ultrasound pulse 23 can be generated so that a deformation is caused in the other slice or the other partial volume 26.

Figure 4:
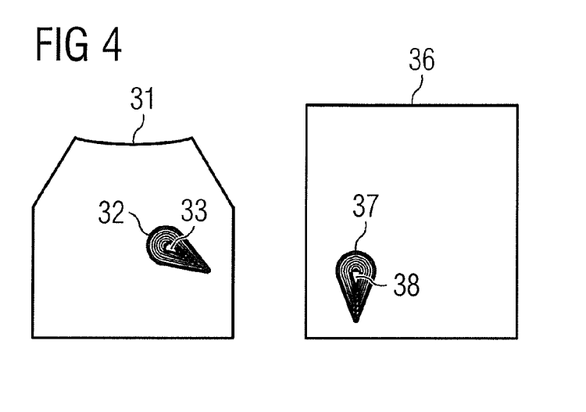
FIG. 4 shows first data and second data that respectively represent a deformation of tissue as a reaction to sound pressure.

FIG. 4 illustrates the registration of US image data and MR image data. A first deformation map 31 is mapped via computation from multiple sets of US image data. The first deformation map 31 represents (with spatial resolution) the spatial displacement of tissue as a reaction to a locally acting force that is generated via ultrasound. The first deformation map 31 can be obtained, for example, by a comparison of two US image data sets, of which one is acquired before and an additional is acquired during or after the deformation caused by sound pressure. A deformation profile 32 shows with spatial resolution the displacement of tissue as a reaction to the sound pressure as it is imaged in the US image data sets. A maximum displacement is present at an image point 33.

A second deformation map 36 is computationally obtained from multiple sets of MR image data. The second deformation map 36 represents with spatial resolution the spatial displacement of tissue as a reaction to a locally acting force that is generated via ultrasound. The second deformation map 36 can be obtained, for example, by a comparison to two MR image data sets, of which one is acquired before and an additional is acquired during or after the deformation caused by sound pressure. A deformation profile 37 shows with spatial resolution the displacement of tissue as a reaction to the sound pressure as it is imaged in the MR image data sets. A maximum displacement is present at an image point 38.

With the image point 33 in the US image data and the image point 38 in the MR image data, a registration point is provided. If a deformation profile is determined, a co-registration can take place using the deformation profiles. Alternatively or additionally, the setting of a local deformation as a landmark for the co-registration can be repeated in order to obtain additional registration points.

Various measures can be used in order to increase the robustness of the co-registration. For example, a threshold comparison can be used. Respectively only regions in which a displacement of the tissue exceeds a threshold can be used in the determination of the deformation maps from US image data sets and MR image data sets. The threshold can be established automatically depending on whether the tissue that is exposed to the sound pressure is relatively soft or relatively rigid.

Figure 5:
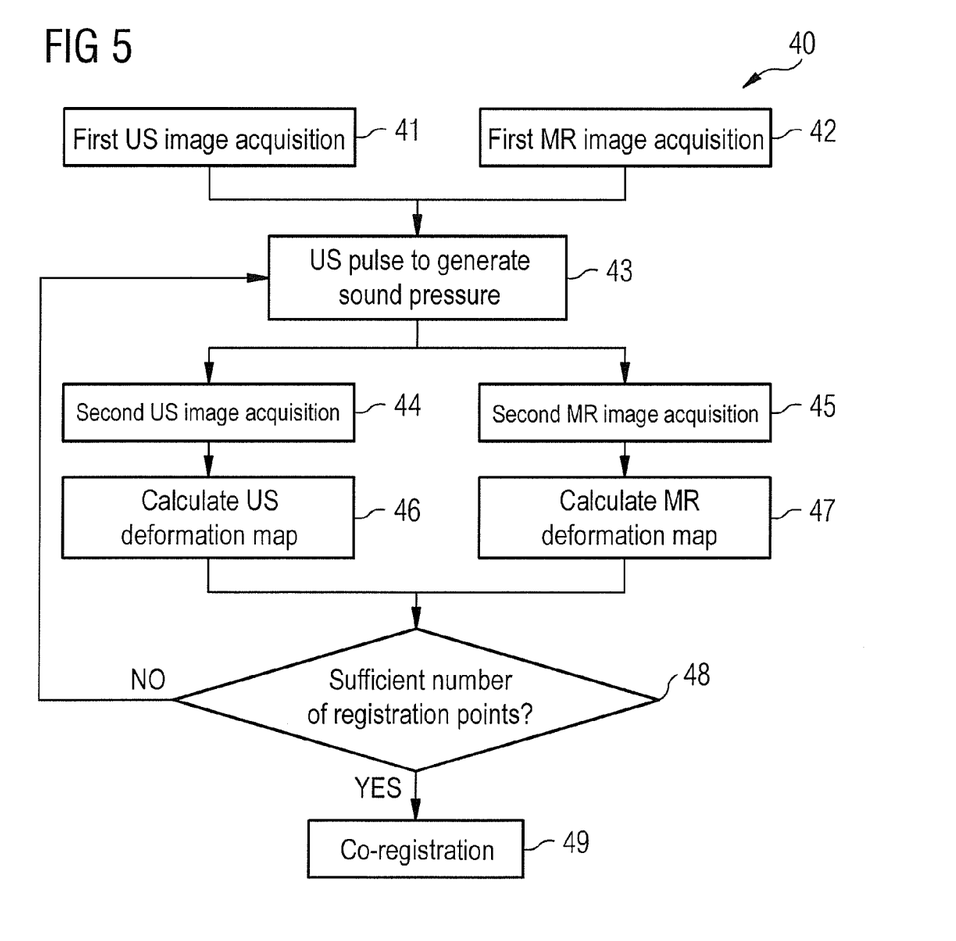
FIG. 5 is a flowchart of a method according to an exemplary embodiment of the invention.

FIG. 5 shows a workflow scheme of a method 40 according to an exemplary embodiment. The method 40 can be executed by the imaging system 1. In the method 40, two US image data sets are acquired in order to determine a displacement of tissue in reaction to the generated sound pressure in a coordinate system of the US image data sets. In the method 40, two MR image data sets are acquired in order to determine a displacement of tissue in reaction to the generated sound pressure in a coordinate system of the MR image data sets.

A first US image acquisition is implemented at 41. A B-image sonography can be implemented at 41. A first examination image can thus be acquired. At 43 an ultrasound pulse is generated in order to cause a local deformation of tissue via sound pressure. A second US image acquisition takes place at 44. The second US image acquisition can take place during the generation of the sound pressure at 43 or after the generation of the sound pressure at 43. The second US image acquisition is then implemented within a time period after the end of the ultrasound pulse that is smaller than a relaxation time of the tissue that was displaced by the ultrasound pulse. In this way it is ensured that the tissue has not yet relaxed into its rest position. The second US image acquisition at 44 can be implemented via ultrasound radiation with which a sonographic tracking takes place. The second US image acquisition at 44 can be implemented with conventional sonographic techniques.

An MR image acquisition also takes place parallel to the US image acquisition. A first MR image acquisition is implemented at 42. The first MR image acquisition can be the acquisition of an overview image with MR. A second MR image acquisition takes place at 45. The second MR image acquisition can take place during the generation of the sound pressure at 43 or after the generation of the sound pressure at 43. The second MR image acquisition is implemented chronologically overlapping with the second US image acquisition. The second MR image acquisition is in any event implemented within a time period after the end of the ultrasound pulse that is shorter than the relaxation time of the tissue that was displaced by the ultrasound pulse. In this way it is ensured that the tissue has not yet relaxed into its rest position.

At 46, first data are calculated depending on a comparison of a first US image data set that was acquired in the first US image acquisition and a second US image data set that was acquired in the second US image acquisition. The first data indicate with spatial resolution the displacement of tissue in the coordinate system of the US image data sets. For example, for this a greyscale image can be calculated that describes with spatial resolution the displacement of the tissue imaged in the US image data sets. At 47, second data are calculated depending on a comparison of a first MR image data set that was acquired in the first MR image acquisition and a second MR image data set that was acquired in the second MR image acquisition. The second data indicate with spatial resolution the displacement of tissue in the coordinate system of the MR image data sets. For example, for this a greyscale image can be calculated that describes with spatial resolution the displacement of the tissue imaged in the MR image data sets. The deformation maps that are determined in this manner in the coordinate system of the MR image data sets and US image data sets can be used for co-registration. For example, a point that has a maximum displacement in the US image data sets according to the first data and a point that has a maximum displacement in the MR image data sets according to the second data can be used as registration points. Multiple points in the first data and the second data can also be used as registration points, for example in the event that a spatially dependent deformation profile was determined with the first data and the second data.

At 48 a check is made as to whether a sufficient number of registration points has already been determined. In the event that a sufficient number of registration points is not yet present, a deformation marker can be dynamically set at an additional point in that sound pressure is exerted on this. The determination of the deformation in the US image data and the MR image data can be repeated. In the check at 48 it can be determined whether a predetermined number of registration points that is selected depending on a parameter count for a co-registration is already present. For a nonlinear co-registration, more than three pairs of registration points must be present in the image data sets acquired with US and MR imaging.

A registration is made at 49. The local deformations generated dynamically by the system in sufficient number via application of sound pressure thereby serve as landmarks for the co-registration. The registration can be a nonlinear co-registration. At least one image data set—for example at least one MR image data set—can be scaled and/or stored nonlinearly.

Figure 6:
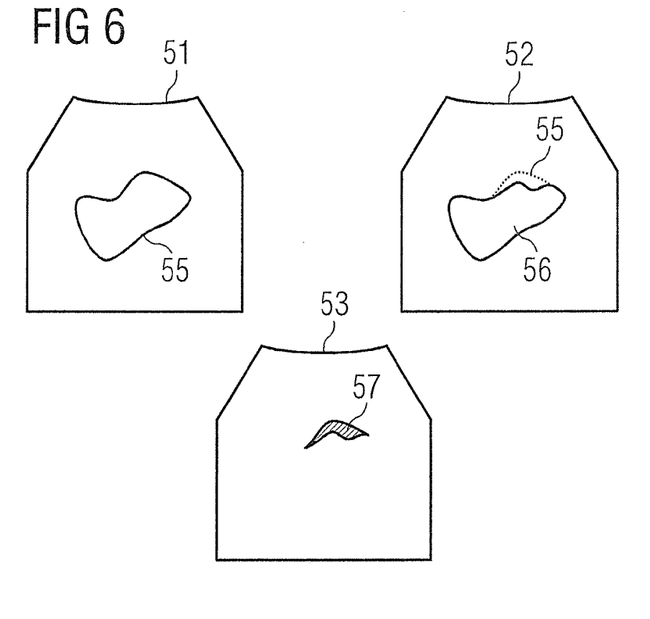
FIG. 6 shows multiple ultrasound image data sets, and first data acquired therefrom.

FIG. 6 shows examples of US image data sets 51, 52 and their processing in the method 40. An image 55 of the tissue is included in a first US image data set 51 that is acquired before a local deformation of tissue that is caused by an ultrasound pulse. An image 56 of the tissue is included in a second US image data set 52 that is acquired after or during the exertion of sound pressure on the tissue to cause a local deformation. The locally applied sound pressure leads to a displacement relative to the original image 55. First data 53 that quantify the displacement can be obtained computationally. A difference image can be calculated, for example. More complex techniques can be used in order to identify a segment 57 in the coordinate system of the US image data sets in which the tissue has been displaced by the ultrasound pulse.

Figure 7:
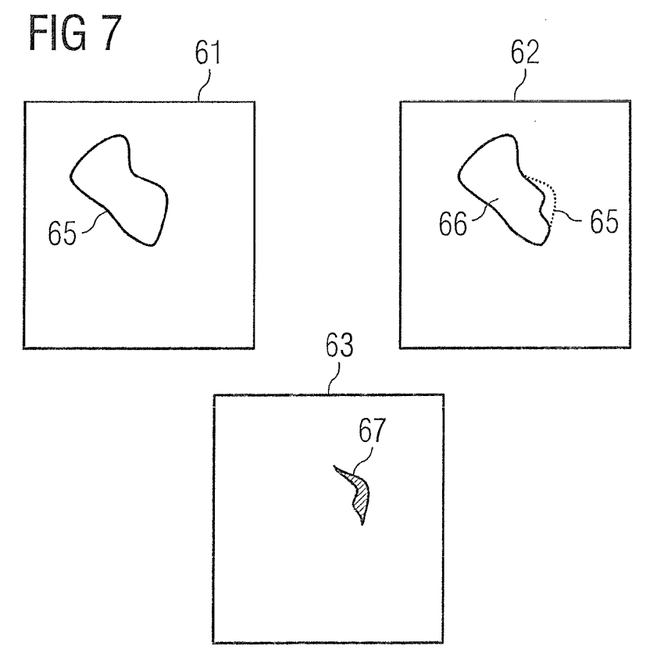
FIG. 7 shows multiple magnetic resonance image data sets, and second data acquired therefrom.

FIG. 7 shows examples of MR image data sets 61, 62 and their processing in the method 40. An image 65 of the tissue is included in a first MR image data set 61 that is acquired before a local deformation of tissue that is caused by an ultrasound pulse. An image 66 of the tissue is included in a second MR image data set 62 that is acquired after or during the exertion of sound pressure on the tissue to cause a local deformation. The locally applied sound pressure leads to a displacement relative to the original image 65. Second data 63 that quantify the displacement can be obtained computationally. A difference image can be calculated, for example. More complex techniques can be used in order to identify a segment 67 in the coordinate system of the MR image data sets in which the tissue has been displaced by the ultrasound pulse.

The computationally determined segments 57, 67 in the images acquired with different imaging modalities can be used for registration.

An identification of tissue that is displaced by locally applied sound pressure can take place not only via acquisition of multiple image data sets and a comparison of the multiple image data sets. The reaction of tissue to sound pressure can also be quantified in a single imaging that, for example, measures the rigidity or viscosity of the tissue. In ultrasound imaging, this can be achieved via sonographic elastography or shear wave imaging. For example, the method described in DE 10 2009 033 286 A1 can be used. A direct imaging of the ultrasound focus in an ultrasound image can also take place as it is described in U.S. Pat. No. 5,769,790. A quantification of the rigidity or viscosity can be achieved in MR imaging, for example via use of diffusion-sensitive MR pulse sequences with a radiation of ultrasound along a diffusion-sensitive direction. Methods that can be used for this are described in WO 2008/067905 A1, for example.

In exemplary embodiments, rigidity or viscosity maps can be acquired with at least one of the imaging modalities. The rigidity or viscosity maps quantify the rigidity or viscosity with spatial dependency in the image data sets acquired with the corresponding imaging modality. The rigidity or viscosity map that was acquired with one imaging modality can be compared with a rigidity or viscosity map that is acquired with the other imaging modality. Alternatively or additionally, the rigidity or viscosity map acquired with one of the imaging modalities can be compared with a deformation map that is calculated from two image data sets acquired with the other imaging modality. Such methods are described with reference to FIG. 8 through FIG. 10.

Figure 8:
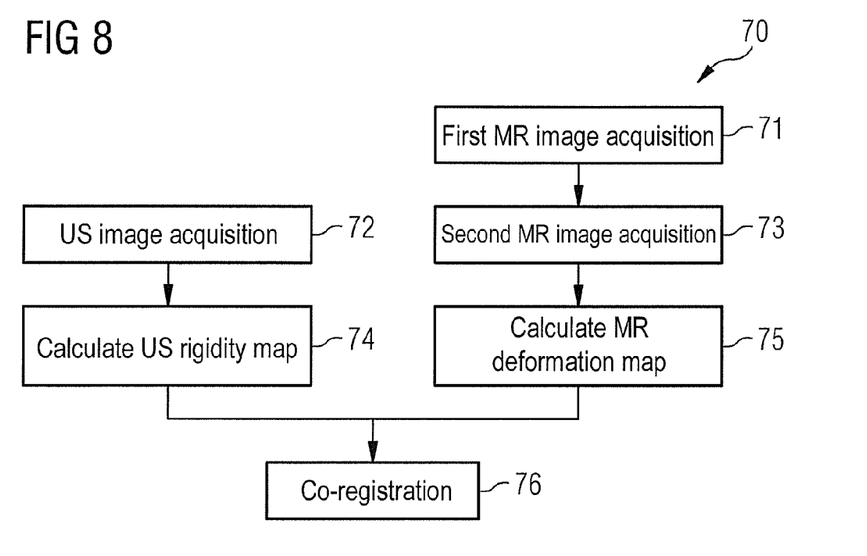
FIG. 8 is a flowchart of a method according to a further exemplary embodiment of the invention.

FIG. 8 shows a workflow scheme of a method 70 according to a further exemplary embodiment. The method 70 can be executed by the imaging system 1.

In the method 70, an acquisition of a US image data set takes place at 72. Sound pressure can thereby be generated that leads to a local deformation of tissue. The acquisition of the US image data set can be implemented with sonographic elastography or shear wave imaging. The method described in U.S. Pat. No. 5,769,790 can also be used in order to sonographically image a focus of the ultrasound pulse. Depending on the US image data set acquired at 72, at 74 spatially resolved information about a rigidity or viscosity of tissue can be calculated. The spatially resolved information about the rigidity or viscosity serve as first data for the co-registration.

In the method 70, at 71 a first MR image data set is acquired before a local deformation of tissue is caused by an ultrasound pulse. A second MR image data set is acquired at 73. The second MR image acquisition can take place during the generation of the sound pressure via the US image acquisition 72 or after the generation of the sound pressure via the US image acquisition 72. The second MR image acquisition takes place before the tissue deformed by the sound pressure relaxes into its rest state. At 75, second data that quantify the displacement of tissue in the coordinate system of the MR image data sets can be calculated from the first MR image data set and the second MR image data set. This can take place as described with reference to FIG. 5 through FIG. 7.

At 76 a registration takes place depending on a comparison of the first data that were determined at 74 and the second data that were determined at 75.

The method 70 can include a check as to whether a sufficient number of reference points is present. Method steps can be repeated selectively in order to generate a sufficient number of registration points by local deformation.

Figure 9:
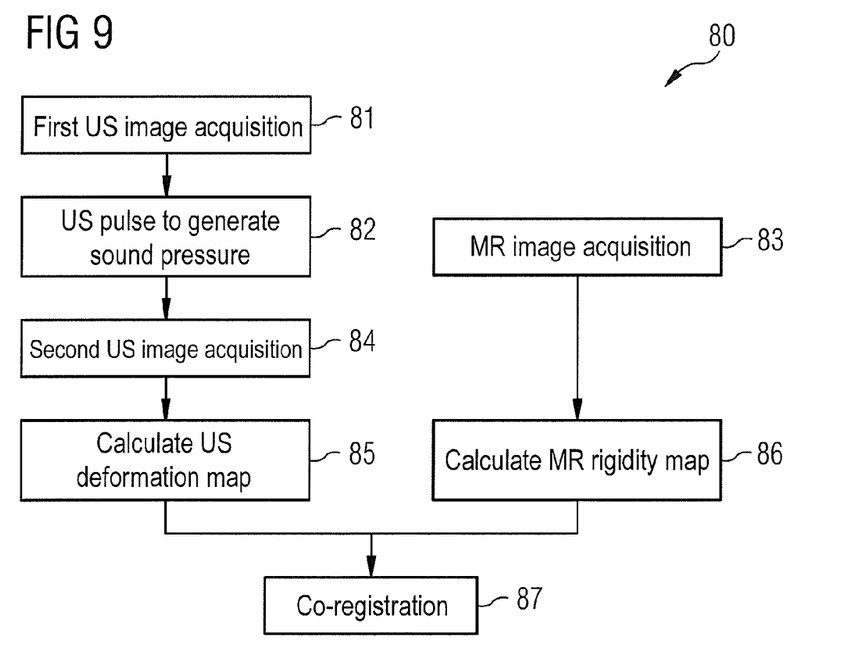
FIG. 9 is a flowchart of a method according to a further exemplary embodiment of the invention.

FIG. 9 shows a workflow scheme of a method 80 according to a further exemplary embodiment. The method 80 can be executed by the imaging system 1.

In the method 80, an acquisition of a first US image data set takes place at 81. At 82 an ultrasound pulse is generated in order to cause a local deformation of tissue. At 84 a second US image data set is acquired. At 85, first data that quantify the displacement of tissue in the coordinate system of the US image data sets are calculated from the first US image data set and the second US image data set. These data serve as first data for the co-registration. Steps 81, 82, 84 and 85 can be implemented as described with reference to FIG. 5.

At 83 an MR image acquisition is implemented in parallel with the generation of the ultrasound pulse at 82. This MR image acquisition can be a diffusion-sensitive MR image acquisition. At 82 the ultrasound pulse can be radiated along a direction along which the MR image acquisition is diffusion-sensitive. The viscous pulse transmission that is caused by the ultrasound pulse allows the imaging of the rigidity or viscosity of the tissue in the MR image acquisition. At 86, the rigidity or viscosity can be determined from the MR image data as a function of the location in the coordinate system of the MR image data. These spatially resolved data serve as second data for the co-registration. The MR data acquisition and evaluation can take place as described in WO 2008/067905 A1.

A co-registration takes place at 87 depending on a comparison of the first data that were acquired at 85 and the second data that were determined at 86. For example, using the variation of the rigidity along the propagation direction of the ultrasound pulse that was determined with MR imaging, it can be determined where the ultrasound pulse strikes the tissue with the lowest rigidity or viscosity. This position can be compared with the position at which the US image data sets exhibit a maximum displacement of the tissue.

The method 80 can include a check as to whether a sufficient number of registration points are present. Method steps can be selectively repeated in order to generate a sufficient number of registration points via local deformation.

Figure 10:
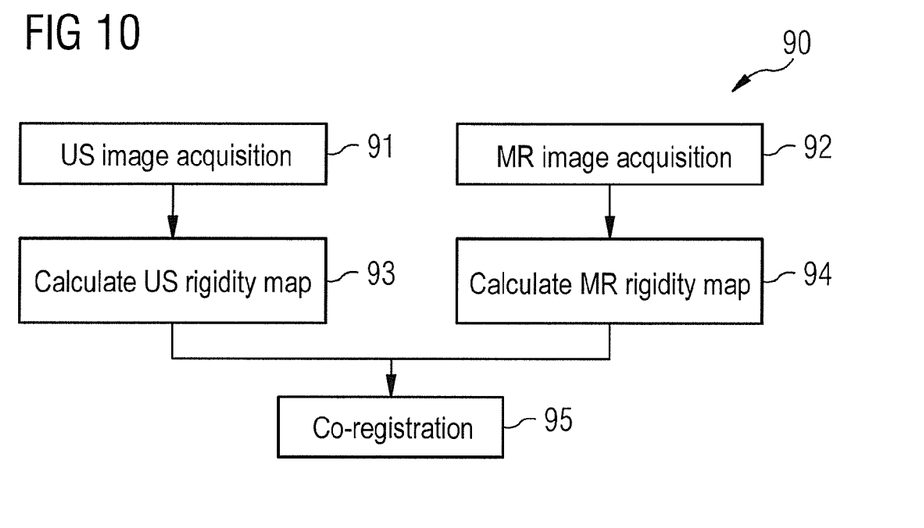
FIG. 10 is a flowchart of a method according to a further exemplary embodiment of the invention.

FIG. 10 shows a workflow scheme of a method 90 according to the further exemplary embodiment. The method 90 can be executed by the imaging system 1.

In the method 90, a US image acquisition with which spatially resolved information about a rigidity or viscosity of the tissue is obtained takes place at 91. An ultrasound pulse is thereby used that leads to a local deformation of the tissue. The acquisition of the US image data set can be implemented with sonographic elastography or shear wave imaging. Depending on the US image data set acquired at 72, at 74 spatially resolved information about a rigidity or viscosity of the tissue can be calculated. The spatially resolved information about the rigidity or viscosity that quantifies the deformation of the tissue as a reaction to radiation pressure serves as first data for the co-registration.

At 92 an MR image acquisition is implemented in parallel with the US image acquisition. This MR image acquisition can be a diffusion-sensitive MR image acquisition. An ultrasound pulse that is used in the US image acquisition can be radiated along a direction along which the MR image acquisition is diffusion-sensitive. The viscous pulse transmission that is caused by the ultrasound pulse allows the imaging of the rigidity or viscosity of the tissue in the MR image acquisition. At 94, the rigidity or viscosity can be determined from the MR image data as a function of the location in the coordinate system of the MR image data. These spatially resolved data serve as second data for the co-registration. The MR data acquisition and evaluation can take place as described in WO 2008/067905 A1.

A registration takes place at 95 depending on a comparison of the first data that were acquired at 93 and the second data that were determined at 94. For example, local minima of the rigidity or viscosity that were determined with the US image acquisition at 91 and the MR image acquisition at 94 can be used as registration points.

The method 90 can include a check as to whether a sufficient number of registration points are present. Method steps can be selectively repeated in order to generate a sufficient number of registration points via local deformation.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for medical imaging, comprising:
   subjecting tissue in a region of an examination subject to sound pressure by applying ultrasound to said region, in order to cause a deformation of said tissue in said region as a reaction to said sound pressure;
   operating an ultrasound imaging device to acquire at least one ultrasound image data set of said region during or after subjecting said tissue to said sound pressure;
   in a processor, determining first data from said at least one ultrasound image data set that represent, with spatial resolution in said at least one ultrasound image set, said deformation of said tissue as a reaction to said sound pressure;
   operating a magnetic resonance imaging device to acquire at least one magnetic resonance image data set of said region during or after said application of said sound pressure to said tissue;

in said processor, determining second data from said at least one magnetic resonance image data set that represent, with spatial resolution in said at least one magnetic resonance image data set, said deformation of said tissue as a reaction to said sound pressure; and in said processor, using the spatially-resolved deformation represented in said first data and the spatially-resolved deformation represented in said second data as respective registration points in said at least one ultrasound image data set and said at least one magnetic resonance image data set, and bringing said at least one ultrasound image data set and said at least one magnetic resonance image data set into registration with each other by causing the respective registration points to spatially coincide with each other.

2. A method as claimed in claim 1 comprising applying said sound pressure to generate a local deformation of said tissue in said region.

3. A method as claimed in claim 1 comprising determining said first data as a representation of a spatially dependent rigidity or viscosity of said tissue.

4. A method as claimed in claim 1 comprising determining said first data as a representation of a spatially dependent displacement of said tissue as a reaction to said sound pressure.

5. A method as claimed in claim 1 comprising determining said second data as a representation of a spatially dependent rigidity or viscosity of said tissue.

6. A method as claimed in claim 1 comprising determining said second data as a representation of a spatially dependent displacement of said tissue as a reaction to said sound pressure.

7. A method as claimed in claim 1 comprising determining each of said first data and said second data as a representation of a spatially dependent rigidity or viscosity of said tissue.

8. A method as claimed in claim 1 comprising determining each of said first data and said second data as a representation of a spatially dependent displacement of said tissue as a reaction to said sound pressure.

9. A method as claimed in claim 1 comprising using said first data and said second data to identify more than three registration points in each of said at least one ultrasound image data set and said at least one magnetic resonance image data set, and wherein the step of bringing said at least one ultrasound image data set and said at least one magnetic resonance image data set into registration with each other comprises implementing a non-linear registration of said ultrasound image data set and said magnetic resonance image data set with each other using said more than three registration points.

10. A method as claimed in claim 1 wherein the step of operating said magnetic resonance imaging device to acquire at least one magnetic resonance image data set comprises operating said magnetic resonance imaging device to acquire a first magnetic resonance image data set and a second magnetic resonance image data set.

11. A method as claimed in claim 10 wherein the step of determining said second data comprises determining said second data by comparing said first magnetic resonance image data set and said second magnetic resonance image data set.

12. A method as claimed in claim 11 comprising operating said magnetic resonance imaging device to acquire said first magnetic resonance image data set before subjecting said tissue to said sound pressure.

13. A method as claimed in claim 1 comprising operating said magnetic resonance imaging device to acquire only one magnetic resonance image data set.

14. A method as claimed in claim 1 wherein the step of operating said ultrasound imaging device to acquire at least one ultrasound image data set comprises operating said ultrasound imaging device to acquire a first ultrasound image data set and a second ultrasound image data set.

15. A method as claimed in claim 14 comprising using said first data and said first data to identify more than three registration points in each of said at least one ultrasound image data set and said at least one magnetic resonance image data set, and wherein the step of bringing said at least one ultrasound image data set and said at least one ultrasound image data set into registration with each other comprises implementing a non-linear registration of said ultrasound image data set and said ultrasound image data set with each other using said more than three registration points.

16. A method as claimed in claim 15 comprising operating said ultrasound imaging device to acquire said first ultrasound image data set before subjecting said tissue to said sound pressure.

17. A method as claimed in claim 1 wherein the step of operating said ultrasound imaging device to acquire at least one ultrasound image data set comprises operating said ultrasound imaging device to acquire a first ultrasound image data set and a second ultrasound image data set.

18. A method as claimed in claim 1 comprising selecting said region of said examination subject to which said sound pressure is applied dependent on factors associated with acquisition of said at least one magnetic resonance image data set.

19. An electronic medical imaging computer comprising:
a first interface that receives at least one ultrasound image data set of a region of an examination subject during or after subjecting tissue in said region to sound pressure that causes a deformation of said tissue in said region as a reaction to said sound pressure;
a processor configured to determine first data from said at least one ultrasound image that represent, with spatial resolution in said at least one ultrasound image set, said deformation of said tissue as a reaction to said sound pressure;
a second interface that receives at least one magnetic resonance image data set of said region during or after said application of said sound pressure to said tissue;
said processor being configured to determine second data from said at least one magnetic resonance image data set that represent, with spatial resolution in said at least one magnetic resonance image data set, said deformation of said tissue as a reaction to said sound pressure; and
said processor being configured to use the spatially-resolved deformation represented in said first data and the spatially-resolved deformation represented in said second data as respective registration points in said at least one ultrasound image data set and said at least one magnetic resonance image data set, and to bring said at least one ultrasound image data set and said at least one magnetic resonance image data set into registration with each other by causing the respective registration points to spatially coincide with each other.

20. A medical imaging system comprising:
an ultrasound source configured to subject tissue in a region of an examination subject to sound pressure by applying ultrasound to said region, in order to cause a deformation of said tissue in said region as a reaction to said sound pressure;

an ultrasound imaging device configured to acquire at least one ultrasound image data set of said region during or after subjecting said tissue to said sound pressure;

a processor configured to determine first data from said at least one ultrasound image data set that represent, with spatial resolution in said at least one ultrasound image set, said deformation of said tissue as a reaction to said sound pressure;

a magnetic resonance imaging device configured to acquire at least one magnetic resonance image data set of said region during or after said application of said sound pressure to said tissue;

said processor being configured to determine second data from said at least one magnetic resonance image data set that represent, with spatial resolution in said at least one magnetic resonance image data set, said deformation of said tissue as a reaction to said sound pressure; and said processor being configured to use the spatially-resolved deformation represented in said first data and the spatially-resolved deformation represented in said second data as respective registration points in said at least one ultrasound image data set and said at least one magnetic resonance image data set, and to bring said at least one ultrasound image data set and said at least one magnetic resonance image data set into registration with each other by causing the respective registration points to spatially coincide with each other.

21. A medical imaging system as claimed in claim 20 wherein said ultrasound source comprises at least one ultrasound transducer of said ultrasound imaging device.

22. A medical imaging system as claimed in claim 20 comprising a control unit in communication with each of said ultrasound source, said ultrasound imaging device and said magnetic resonance imaging device, and configured to operate said ultrasound source, said ultrasound imaging device and said magnetic resonance imaging device respectively, to apply said sound pressure, acquire said ultrasound image data set, and acquire said magnetic resonance image data set.

\* \* \* \* \*